United States Patent
Chung et al.

(10) Patent No.: US 6,342,384 B1
(45) Date of Patent: Jan. 29, 2002

(54) PRODUCTION OF ADENOVIRAL VECTORS USING SERUM-FREE SUSPENSION CELL CULTURE IN A HOLLOW FIBER SYSTEM

(75) Inventors: Leland W. K. Chung, Lovingston; Thomas A. Gardner, Charlottesville; Chinghai Kao, Charlottesville; Song-Chu Ko, Charlottesville, all of VA (US)

(73) Assignee: The University of VA Patent Foundation, Charlottesville, VA (US)

( * ) Notice: Subject to any disclaimer, the term of this patent is extended or adjusted under 35 U.S.C. 154(b) by 0 days.

(21) Appl. No.: 09/193,134

(22) Filed: Nov. 17, 1998

Related U.S. Application Data
(60) Provisional application No. 60/097,433, filed on Aug. 21, 1998.

(51) Int. Cl.[7] .................................................. C12N 7/02
(52) U.S. Cl. ..................................... 435/235.1; 435/239
(58) Field of Search ............................... 435/235.1, 352, 435/364, 366, 369, 383, 239

(56) References Cited

U.S. PATENT DOCUMENTS

| | | | | |
|---|---|---|---|---|
| 4,724,146 A | * | 2/1988 | Kino et al. ..................... | 424/89 |
| 5,219,752 A | * | 6/1993 | Takazawa et al. ...... | 435/240.25 |
| 5,304,483 A | * | 4/1994 | Takeuchi et al. ........ | 435/240.25 |
| 5,498,537 A | * | 3/1996 | Bresler et al. ............ | 435/235.1 |
| 5,773,289 A | * | 6/1998 | Samulski et al. ......... | 435/320.1 |

OTHER PUBLICATIONS

Cote et al., Biotechnol. Prog., 13:709–714, Dec. 1997.*
Katayama et al., Bone Marrow Transplantation, 19:283–287, 1997.*

* cited by examiner

Primary Examiner—Brenda Brumback
(74) Attorney, Agent, or Firm—Pennie & Edmonds LLP

(57) ABSTRACT

The present invention relates to methods for the production of high titers of serum-free lytic viruses in a hollow fiber cartridge capillary system. The invention further relates to methods of infecting target cells at high multiplicity and for producing high concentrations of transduced target cells.

2 Claims, 3 Drawing Sheets

CsCl banding of adenovirus (see the lower band from the bottom, which contains purified adenovirus).

PRODUCTION OF ADENOVIRAL VECTORS USING SERUM-FREE SUSPENSION CELL CULTURE IN A HOLLOW FIBER SYSTEM

The application claims the benefit under 35 U.S.C. § 119(e) of provisional Application No. 60/097,433, filed on Aug. 21, 1998, which is hereby incorporated by reference in its entirety.

INTRODUCTION

The present invention relates to methods for the production of high titers of serum-free lytic viruses in a hollow fiber cartridge capillary system. The invention further relates to methods of infecting target cells at high multiplicity and for producing high concentrations of transduced target cells.

BACKGROUND OF THE INVENTION

Gene therapy is defined as the use of genetic material for therapeutic purposes. Patients diagnosed with inheritable genetic diseases can be, in principle, treated by the introduction of a therapeutic gene in replacement of an aberrantly functioning gene. For example, aberrant functioning of the adenosine deaminase (ADA) gene, the gene which encodes the low density protein in familial hypercholesterolemia and the chloride transporter gene in Cystic Fibrosis can be corrected by the introduction of therapeutic genes.

There also are examples where overexpression of an oncogene, or the lack of expression of a tumor suppressor, could be the molecular basis of cancers. Under these conditions, both corrective as well as cytoreductive strategies have been used to introduce genetic materials, either to repair the damage that caused aberrant growth of the cancer cells, or the use of a cytoreductive strategy to introduce various forms of toxic genes that can control the growth of cancer cells. For these reasons, gene therapy has become increasingly popular for the treatment of inheritable genetic diseases, as well as cancer and cardiovascular diseases. As of May 12, 1998, more than 212 gene therapy protocols have been approved by the Recombinant DNA and Advisory Committee (RAC) of the National Institute of Health (NIH) since the first human ADA deficient patients receives such therapy in 1990. In the approved protocols by the RAC of the NIH, 147 out of 212 approved protocols are for the treatment of cancer using a gene therapeutic approach.

The current invention describes a novel method whereby high yields ($6 \times 10^{12}$ virus particles) of lytic-viral vectors can be produced consistently and reproducibly. This method is an improvement over the current method for the production of clinical therapeutic grade viral vectors because the entire production process is performed in a self-contained system and in a serum-free condition using a hollow fiber bioreactor system. This new technique has the further advantage of allowing scale-up to a level that is not economically or physically feasible using the current technique.

Prior to the instant invention, similar techniques were performed only on retroviral vectors, and not on lytic-viral vectors, as disclosed in the present application. See, U.S. Pat. No. 5,498,537, entitled "Serum-free production of packaged viral vector".

The present invention significantly differs from what was previously known in the art. For example, the present invention relates to the production of lytic-viral vectors whereas previously, only methods of utilizing budding retroviral vectors were known. A further difference between what was previously known in the art and the instant invention is that previously, PA 117 derived packaging cells were principally used as hosts for the production of retroviral vectors, whereas the present application uses human fetal kidney 293 cells for the production of lytic-viral vectors. Although artificial capillary hollow fiber cartridge systems were previously known in the art, it was not until the instant invention that completely serum-free medium was used to store cells. Prior to the instant invention, packaged cell lines typically were cultured initially in the presence of bovine serum-containing culture medium, and then subsequently either continued in serum-containing media or the serum-containing medium was replaced with a serum-free medium. As noted above, the instant application describes a 293 cell culture that has been adapted to grow in serum-free medium, and can be stored under serum-free conditions with 10% DMSO. This condition is favorable in that the culture cells can be retrieved quickly from liquid nitrogen, and subjected to culture immediately, without needing additional adaptation steps. Further, using this technique, cell cultures have good viability and grow under completely serum-free conditions. This allows the viral infection to occur quickly and reproducibly and avoids the potential contamination from serum preparations. Previously, retroviral-producing cell lines which were capable of producing retroviruses before seeding the capillary system were used. The current methodology, to the contrary, describes the use of 293 cells grown under serum-free conditions at early onset that are subjected to infection by the master copy of the lytic virus after growth in the capillary system has been established to an appropriate level of lactate production.

Further, prior methods involved harvesting retrovirus from the medium of the hollow fiber cartridge system where the budding retroviruses reside, whereas the current methods involve the harvesting of adenoviruses from both the cells as well as the medium within the extracapillary space (ECS).

The large scale production of recombinant adenoviruses is based mostly on a book chapter written by Graham, F. L. and L. Prevec (1991). *Manipulation of adenovirus vectors*. Clifton, N.J., The Humana Press, inc. and updated article by Frank, F. L. and Prevec, L. Methods for construction of adenovirus vectors, Molecular Biotechniques, 3:207–220, 1995.

SUMMARY OF THE INVENTION

The present invention generally relates to lytic viruses. More particularly, the invention is directed to a novel method for the production of lytic viruses using a capillary system. After infecting host cells with a lytic virus, the infected host cells are cultured and the lytic virus is harvested from the culture medium.

In a preferred embodiment, the lytic viruses of the invention are either replication defective or replication competent. In other embodiments, the lytic viruses of the invention include, but are not limited to, adenoviruses, parvoviruses, adeno-associated viruses, herpes simplex viruses, polio viruses or papillomaviruses. In further embodiments of the invention, the host cells include, but are not limited to, 293 cells, CCL81.1 cells, Vero cells, HEL cells or BHK cells.

In a further preferred embodiment, the capillary system is a hollow fiber cartridge system. In yet other embodiments of the invention, the virus is a viral vector, and, further, the viral vector encodes a therapeutically effective product. Another preferred embodiment of the invention involves host cells which have been adapted to grow and be stored under serum-free conditions. Specifically, an example of a serum-free condition is storage of host cells in 10% DMSO.

In another embodiment, viral infection is carried out at a cellular lactate production rate of 500 mg/day. Furthermore, viruses are harvested at a cellular lactate production rate of between 1000 and 1500 mg/day. A further embodiment of the invention relates to host cells which are substantially isolated from the cellular material. In still a further embodiment of the invention, the viruses are harvested from the extracapillary space of the capillary system.

DETAILED DESCRIPTION OF THE INVENTION

Figure 1:
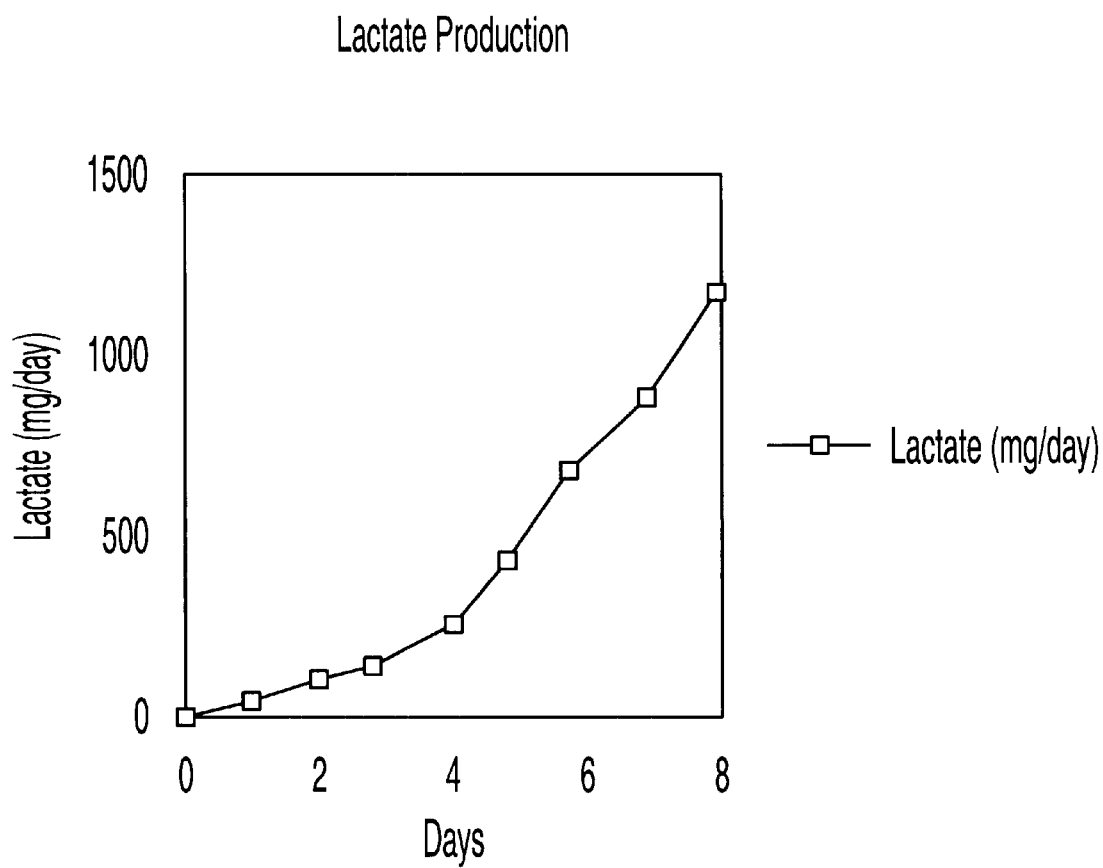
FIG. 1 shows that the production of adenovirus was followed by lactate production by 293 cells. Lactate is a metabolic indicator of 293 cells. Lactate production serves as an index in determining when the cell cultures should be harvested using the hollow fiber cartridge system.

The present invention describes a two-step system wherein host cells, such as, for example, human kidney 293 cells have been adapted to grow under serum-free conditions in suspension. These cells are used in a hollow fiber cartridge system where a master copy of a lytic virus was used to infect the 293 cells in culture at the time when 293 cells were grown in the hollow fiber cartridge system. Preferred lytic viruses include, but are not limited to, adenoviruses, parvoviruses, such as adeno-associated virus (AAV), papillomavirus, and herpes simplex viruses (e.g. HSV-1). Host cells which can be used in accordance with the invention include but are not limited to 293 cells (e.g., for adenovirus and adeno-associated virus), Vero (African green monkey ATCC #CCL81) cells, other permissive cells such as HELs or BHKs, or complementing cell lines are usually used to propagate HSV-1 accessory or essential gene deletion viruses. These cell lines can be adapted gradually to serum free conditions and using the procedures described in Section 6, below. CCL 81.1 cells, a variant of original CCL81 adapted to grow under serum free condition, is available through the ATCC catalog.

In order to insure success of viral production, viral infection is achieved by allowing the master copy of the lytic virus to infect the 293 cells at the correct level of lactate production rate.

As used herein, lytic virus refers to any virus that is released from the host through the process of cell lysis, as opposed to, for example, through budding.

The invention encompasses production of both replication deficient viruses and replication competent viruses. In the case of replication deficient viruses, a variety of suitable competent host cell which provides the required replication factor may be used to grow the viral vectors in accordance with the invention.

Although the idea of producing lytic viruses using a suspension cell culture under serum-free condition medium is not a new concept, the practice of this concept, however, has been generally unsuccessful in past years. A significant aspect of this invention is that by adopting the growth of 293 cells under complete serum-free medium, and by the storage of 293 cells in 10% DMSO, it allows us to retrieve 293 cells quickly from the freezer, and grow them under serum-free conditions successfully and reproducibly. This 293 cell subline adapted by serum-free growth conditions is susceptible to viral infection, provided that ideal cell culture conditions are provided. To accomplish this, we have experimented on an empirical basis using varying conditions to allow the infection of lytic virus to occur in the host producing cells efficiently. After much of the empirical experimentation, we discovered that by allowing the master copy of the lytic virus to infect the 293 cells at the appropriate lactate level, we are able to produce high titers reproducibly by the 293 cell line that was grown under serum-free conditions in the hollow fiber cartridge system.

Capillary systems that can be used in accordance with the invention include, but are not limited to, Cellmax® SPS (e.g., Cat. No. 400-023; Cat. No. 4023-00) and MPS systems from Cellco Inc. (Laguna Hills, Calif.). These systems are commercially available and can be ordered through Gibco-BRL (Gaithersburg, Md.).

The following examples are included for illustrative purposes and are not intended to limit the scope of the invention.

EXAMPLE

Production of Serum-free 293 Cells

The human fetal kidney 293 cell line is obtained from American Type Culture Collection (ATCC). This cell line is subsequently conditioned under serum-free medium using a conventional step-down method, wherein the 293 cells will grow under gradually decreasing serum concentrations through in vitro cell passages. After this downshift of serum, a 293 subline is generated, which is capable of growing actively in IS 293 medium (obtained from Irvine Scientific) successfully. The 293 subline also can be frozen under serum-free medium with 10% DMSO, and can be retrieved quickly from the deep freezer for convenient culture in liquid culture under serum-free conditions or directly into the capillary system. We typically retrieve 293 cells from liquid nitrogen which has been stored in IS media with 10% DMSO. This cell line is then thawed quickly in a 37° C. water bath and washed with IS media and then grown in suspension culture under the following conditions. First, roughly about $5 \times 10^7$ 293 cells (1 vial) will be cultured in a 100 ml liquid culture, in the absence of serum, and in the presence of IS 293 medium (Irwin Scientific). Further, the lactate of the medium is monitored daily. At 3 to 4 days after initiating this culture, the cells are counted and $5 \times 10^7$ cells are inoculated into the luer-lock port of the capillary system. The cells are injected slowly into the extra-capillary space (ECS) to avoid damage to the cells.

Figure 2:
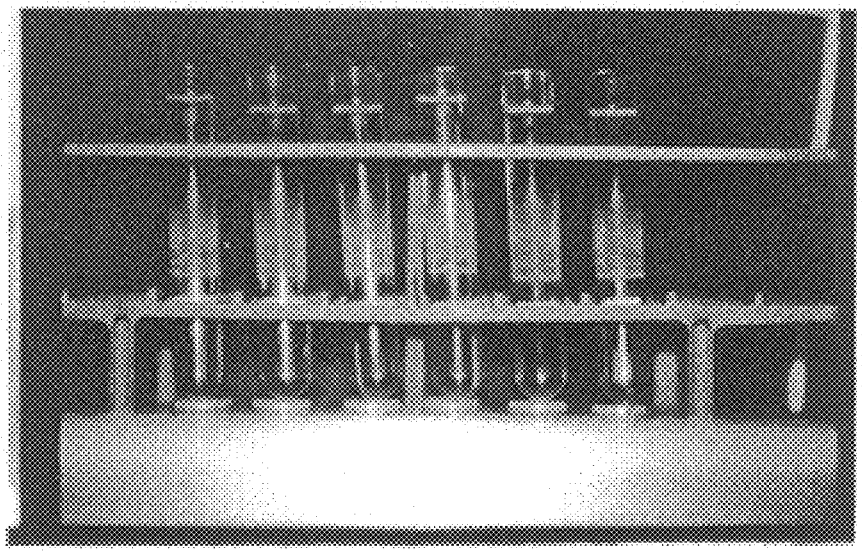
FIG. 2 is a typical pattern of cesium chloride banding of the adenoviruses produced from the hollow fiber cartridge system. The clear adenoviral band can be detected at the buoyant density.
Figure 3:
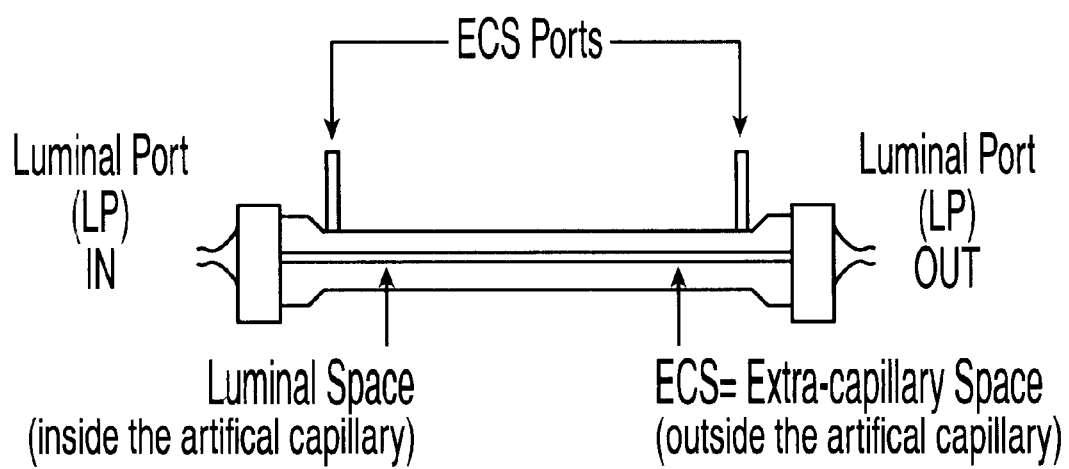
FIG. 3 is a schematic representation of a capillary system.

After this initial growth phase is established and the cells are seeded into the capillary system, the lactate levels are monitored to assess the growth rate. Viral infection is performed at 500 mg/day lactate production. At this time, the virus can be harvested from within the extra capillary space. Thirty milliliters of fluid are removed from the extracapillary space. This volume is then purified using CsCl banding. FIG. 2 demonstrates a typical banding pattern after the initial step gradient centrifugation. CsCl purification is needed for more efficient adenoviral production because crude cellular lysates often clog up the pores on the membrane of the capillary system and interfere with gas exchanges. The efficiency of adenoviral infection, as assessed by β-galactosidase and thymidine kinase activities, is comparable between the adenoviruses produced by the hollow fiber cartridge system and those produced by conventional systems.

TABLE 1

Basic comparison of conventional and hollow fiber systems
for the large scale production of recombinant adenovirus

| | Method | |
|---|---|---|
| Parameter | Conventional Method 200 T175s | Hollow Fiber System 4 2100 cm² cartridges |
| Total Personhours | 55 hours | 6 hours |
| Volume of media which virus is recovered from | 5000 ml | 120 ml |
| Supply Costs | Same | Same |
| Personnel Costs | Large | Minimal |
| Incubator Space Allocation | Large | Minimal |
| Storage Space Allocation | Large | Minimal |
| Serum (FBS) | Yes | No |
| Relative Yield of adenovirus | Same | Same |
| Airborne adenovirus | Large | Minimal |
| Production of bioharardous waste | Large | Minimal |

Table 2, below, indicates the dates of 57 runs that were conducted in manufacturing 14 different forms of adenoviruses using hollow fiber cartridge systems. The stars (*) represent failures from 4 batches of contamination in the indicated forms of adenovirus production.

TABLE 2

| Viral Name | Set-up Date | # of Batch to date |
|---|---|---|
| Ad-CMV-TK | 8/4/97 | *2(#1-LPS) |
| | 5/22/98 | 4(#16-SPS) |
| Ad-CMV-p53 | 7/13/98 | 1(#20-SPS) |
| Ad-CMV-p21 | 7/20/98 | 1(#21-SPS) |
| Ad-CMV-βGal | 8/5/97 | 2(#2-SPS) |
| | 2/23/98 | 4(#9-MPS) |
| Ad-RSV-TK | 10/14/97 | 5(#5-SPS) |
| | 4/15/98 | 2(#12-MPS) |
| Ad-RSV-CD | 8/12/97 | 6(#4-SPS) |
| | 4/15/98 | 2(#12-MPS) |
| Ad-OC-TK | 5112/97 | *1(#3-SPS) |
| | 3/20/98 | *4(#11-SPS) |
| | 5/22/98 | 1(#15-SPS) |
| Ad-OC-βGal | 9/4/97 | 4(#6-SPS) |
| Ad-OC-Ela | 6/2/98 | 4(#17-SPS) |
| Ad-PSA-TK | 12/1/97 | 4(#7-SPS) |
| Ad-PSA-Ela | 12/7/97 | 4(#8-SPS) |
| Ad-CEA-TK | 2/23/98 | 2(#10-SPS) |
| Ad-CMV-TK-CD-p53 | 4/30/98 | *1(#14-SPS) |
| | 6/30/98 | 1(#14-SPS) |
| Ad-lac8-luc | 7/2/98 | 1(#18-SPS) |

Table 3 below is a comparative chart regarding the conventional and serum-free cell suspension production of adenoviruses under hollow fiber cartridge systems. We compared the cost of labor, the requirement of incubator space, the supplies, and the environmental waste generated by the culture between the conventional method, and this invention for a simulated single large scale production run.

TABLE 3

| | Old Technique* | New Technique* | Comparison Old:New |
|---|---|---|---|
| WASTE | | | |
| Biological Hazards | 27,500 cubic inches | 360 cubic inches | 75:1 |
| STORAGE SPACE | | | |
| Plasticware | 23,222 cubic inches | 360 cubic inches | 65:1 |
| INCUBATORS | | | |
| Number | 5 | 1 | 5:1 |
| PERSONHOURS (one experienced technician) | | | |
| Preparation of 293 cells | 8 hours (200 p100's) | 1 hour (2 × 500cc liquid culture) | |
| Media Change | 12 hours (4 hours per 3 changes) | .33 hour (1 change) | |
| Seeding cells for production Chambers | 12 hours (200 T175's) | 1 hour (4 Cartridges) | |
| Media Change & Viral Innoculation | 8 hours (200 T175's) | 1 hour (4 Cartridges) | |
| Harvest of Cells | 8 hours | 1.66 hours | |
| Totals | 55 hours | 6 hours | 9:1 |
| SUPPLIES($) | | | |
| Plasticware | 900 | 1200 | |
| Media | 200 | 480 | |
| Serum | 600 | 0 | |
| Totals | 1700 | 1680 | 1:1 |
| Estimated Totals with Labor | 30,000 | 3,000 | 10:1 |

*Old technique 200 T175's to produce 2.4 × 10 13 v.p.
New Technique 4 Cartridges 2.4 × 10 13 v.p.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foreign description and accompanying drawings. Such modifications are intended to fall within the scope of the appended claims.

What is claimed is:

1. A method for the production of lytic virus, comprising
   (a) inoculating host cells into a serum-free liquid medium in a capillary system,
   (b) infecting the host cells with lytic virus,
   (c) culturing the infected host cells, and
   (d) harvesting the lytic virus from the culture medium, wherein said viral infection is carried out at a cellular lactate production rate of 500 mg/day.

2. A method for the production of lytic virus, comprising
   (a) inoculating host cells into a serum-free liquid medium in a capillary system,
   (b) infecting the host cells with lytic virus,
   (c) culturing the infected host cells, and
   (d) harvesting the lytic virus from the culture medium, wherein the virus is harvested at a cellular lactate production rate of between 1000 and 1500 mg/day.

* * * * *